United States Patent [19]

Lee

[11] Patent Number: 4,609,399

[45] Date of Patent: Sep. 2, 1986

[54] SUBSTITUTED 4,6-ALKOXY PYRIDINECARBOXYLATE COMPOUNDS AND HERBICIDAL USE

[75] Inventor: Len F. Lee, St. Charles, Mo.

[73] Assignee: Monsanto Company, St. Louis, Mo.

[21] Appl. No.: 668,790

[22] Filed: Nov. 6, 1984

[51] Int. Cl.$^4$ ................ A01N 43/40; C07D 213/80
[52] U.S. Cl. ........................................ 71/94; 546/296
[58] Field of Search ........................... 546/296; 71/94

[56] References Cited

U.S. PATENT DOCUMENTS 3,629,270 12/1971 Gante ................................. 546/283
3,705,170 12/1972 Torba ..................................... 71/94

Primary Examiner—Henry R. Jiles
Assistant Examiner—Dale A. Bjorkman
Attorney, Agent, or Firm—James C. Bolding

[57] ABSTRACT

Disclosed herein are 4,6-dialkoxy 3-pyridine carboxylic acids and their derivatives which are useful as herbicides and herbicide intermediates.

12 Claims, No Drawings

SUBSTITUTED 4,6-ALKOXY PYRIDINECARBOXYLATE COMPOUNDS AND HERBICIDAL USE

This invention relates to a new class of substituted pyridinecarboxylic acid derivatives having a wide range of activity as herbicides and as precursors for herbicides.

Pyridine derivatives have, for many years, been investigated for use in the biological sciences. For example, 2,6-bis(trifluoromethyl)-4-pyridinols have been found useful as herbicides and fungicides as disclosed in U.S. Pat. No. 3,748,334. Such compounds are characterized by substitution in the 4-position by a hydroxyl radical. In addition to the hydroxyl radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO patent No. 44,262 there are disclosed 2,6-dialkyl-3-phenylcarbamyl-5-pyridinecarboxylates and -5-cyanocompounds useful as herbicides. There is no disclosure of the 2-haloalkyl radicals nor any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4 position is occupied by a silver salt, U.S. Pat. No. 1,944,412 discloses that such compounds have been utilized in the production of X-ray pictures with intraveneous injection of such compounds. None of the above-mentioned prior art discloses pyridines containing both a trifluoromethyl radical at the 2-position and a carboxyl radical at the 3-position.

BRIEF DESCRIPTION OF THE INVENTION

It is an object of this invention to provide herbicidal methods and compositions utilizing the novel pyridines of this invention.

Another object of this invention is to provide novel methods for preparing the novel compounds of this invention and novel intermediates useful therein.

The novel compounds of this invention are useful as herbicides or intermediates which can be converted to herbicides and represented by the generic formula

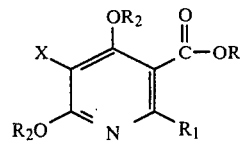

wherein:

R is selected from the group consisting of hydrogen, lower alkyl, lower alkenyl, lower alkynyl, haloalkyl, haloalkenyl.

$R_1$ is fluorinated methyl and chlorofluorinated methyl;

$R_2$ is selected from hydrogen and lower alkyl radicals; and

X is selected from

H

in which $R_3$ is hydrogen, lower alkyl, lower alkenyl, lower alkynyl, or haloalkyl,

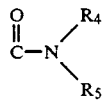

in which $R_4$ and $R_5$ are independently selected from hydrogen and lower alkyl $C\equiv N$;

lower alkyl;

lower alkoxyalkoxymethyl haloalkyl;

lower cyanoalkyl; and carbalkoxyalkyl.

The term "fluorinated methyl" means herein methyl having one or more fluorine atoms attached thereto, including a radical wherein all hydrogen atoms are replaced by fluorine. The term "chlorofluorinated methyl" means herein a methyl radical having at least one hydrogen replaced by fluorine and at least one other hydrogen replaced by chlorine.

The term "lower alkyl" means herein means both straight and branched alkyl chain radicals having 1 to 7 atoms which include, but are not limited to, ethyl, methyl, n-propyl, 1-ethylpropyl, 1-methylpropyl, n-butyl, 2,2-dimethylpropyl, pentyl, isobutyl, isopropyl.

The terms "lower alkenyl" and "lower alkynyl" herein mean alkenyl and alkynyl groups having 3 to 7 carbon atoms wherein the unsaturation is remote from the moiety attaching the lower alkenyl or alkynyl group to the pyridine ring. Examples of such alkenyl groups include 2-propenyl, 2-butenyl, 3-butenyl, 2-methyl-2-propenyl, and the like. Examples of such lower alkynyl groups include 2-propynyl, and so forth.

The term "haloalkyl" is intended to mean lower alkyl radicals substituted with one or more halogen atoms. The term haloalkenyl is intended to mean lower alkenyl radicals substituted with one or more halogen.

DETAILED DESCRIPTION OF THE INVENTION

Route A below schematically depicts a method whereby the pyridine monocarboxylate compounds of this invention may be prepared from compounds which are readily available commercially. In Route A, an acetonedicarboxylic acid diester of the formula shown in which R is hydrogen or lower alkyl is reacted with a fluorinated or chlorofluorinated acetonitrile wherein the hydrogens of the nitrile are fully replaced by fluorine or one of the hydrogens is replaced by fluorine and the other two hydrogens are replaced by one fluorine and one chlorine or by two chlorines in the presence of a base. Examples of suitable bases are lithium diisopropylamide, potassium t-butoxide, sodium, aqueous sodium acetate, and the like. The result of this reaction is a pyridine monocarboxylate compound (A).

The 4,6-dihydroxy pyridine compounds shown in Formula A may be converted to a 4-alkoxy compound of this invention (Formula B) by alkylation with an alkyl halide in the presence of a base. Alkali metal carbonates or hydroxides, amines, and the like, are examples of suitable bases which promote the alkylation reaction.

The pyridinemonocarboxylate compounds of the present invention having an alkoxyalkoxymethyl group at the 5-position (Formula F) may be prepared by reacting the anion of formula E with an appropriate alkoxyalkoxymethyl halide. The pyridinemonocarboxylate compounds of the present invention having a halomethyl group at the 5-position (Formula G) may be prepared by treatment of the compounds of formula F with an appropriate Lewis acid, preferentially a metallic halide such as titanium (IV) halide or zinc (II) halide. Preparation of pyridinemonocarboxylate compounds of this invention having a cyanomethyl or carbalkoxymethyl group at the 5-position from the compounds of formula G is well within the skill of the art and described in examples herein.

Preparation of carboxylic acids from the corresponding esters and vice versa is well within the skill of the art. Likewise, preparation of the amide, nitrile, and other compounds of this invention is achieved by well-known methods understood by workers in the art.

ROUTE A

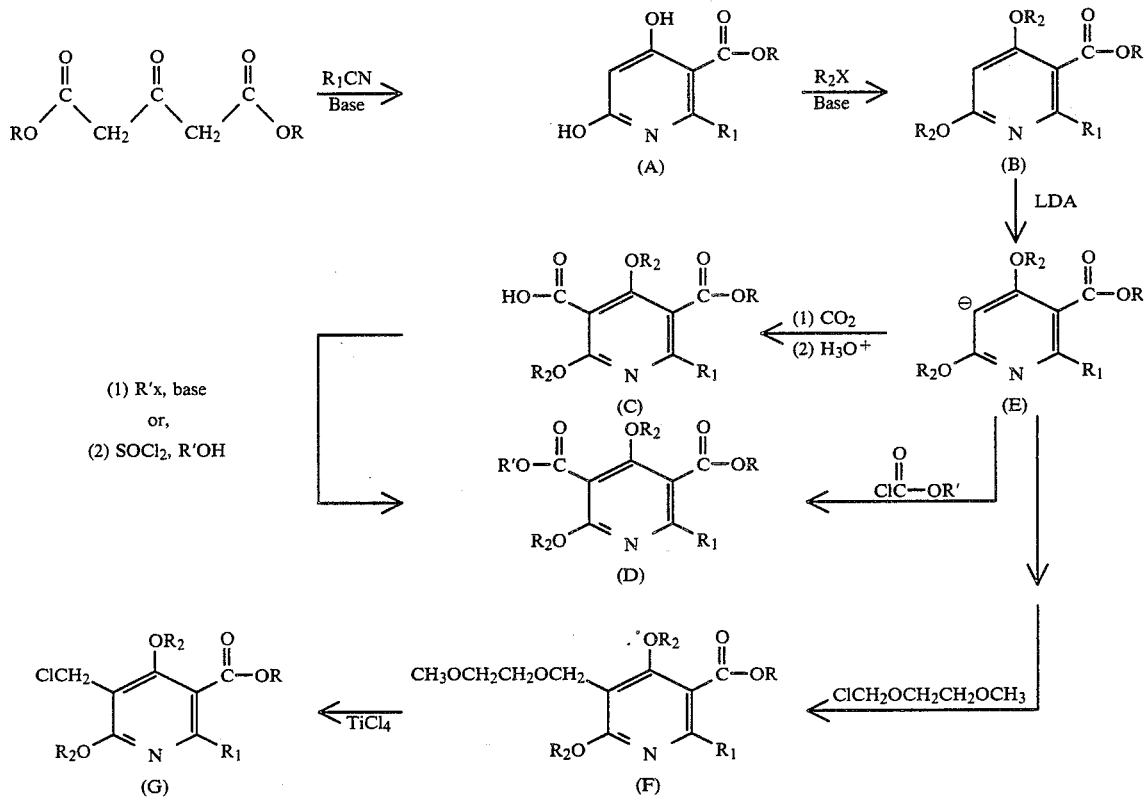

Following preparation of the 4,6-dialkoxy pyridine monocarboxylate intermediate compounds of Formula B, pyridine dicarboxylate compounds of the present invention having a carboxylic acid group at the 5-position (Formula C) may be prepared by first reacting compounds of formula B with a strong base such as lithium diisopropylamide (LDA) in an appropriate solvents such as tetrahydrofuran (THF) or 1,2-dimethoxyethane (DME) to generate an anion of formula E; the anion of formula E then is reacted with carbon dioxide and the resulting carboxylic acid salt is acidified with aqueous hydrochloric acid. Alternatively dicarboxylate compounds of Formula D may be prepared by reacting the anion of formula E with an alkyl chloroformate.

A better appreciation of the present invention will be gained by reference to the following Examples.

As used throughout the specification, including the Examples, the following abbreviations have the following meanings:

LDA—lithium diisopropylamide
THF—tetrahydrofuran
DME—1,2 - dimethoxyethane
DMF—N,N-dimethylformamide
HPLC—high pressure liquid chromatography
TLC—thin layer chromatography
n-BuLi—n-Butyl lithium
DMSO—dimethyl sulfoxide

PREPARATION OF 4,6-DIHYDROXY PYRIDINE MONOCARBOXYLATES

The following Examples 1 and 2 illustrate the preparation of 4,6-dihydroxy pyridine monocarboxylates by reaction of an acetonedicarboxylate with a fluorinated acetonitrile.

EXAMPLE 1

Ethyl 4,6-dihydroxy-2-(trifluoromethyl)-3-pyridinecarboxylate (a) Using NaOAc as base To a mechanically stirred mixture of 201 g (1.0 mol) of diethyl acetonedicarboxylate, 95 g of sodium acetate, 100 ml of water and 200 ml of ethanol at 55° C. was passed 89 g of trifluoroacetonitrile in 15 hours. The reaction temperature was raised to 70° C. and additional 15 g of trifluoroacetonitrile was passed to the reaction mixture in 15 hours. The reaction mixture was poured into a mixture of 100 ml concentrated hydrochloric acid and 600 ml of water. The precipitate was collected and recrystallized from acetone-chloroform to give 130.3 g (51.9%) of product: mp 217°–220° C.

Anal. Calc'd. for $C_9H_8F_3NO_4$: C, 43.03; H, 3.21; N, 5.58; Found: C, 43.01: H, 3.22: N, 5.55.

(b) Using potassium t-butoxide as base

To a mechanically stirred mixture of 335 g (2.98 mol) of potassium t-butoxide and 1.25 L of THF was added 575 g (2.84 mol) of diethyl acetonedicarboxylate at such a rate that the reaction temperature was maintained below 60° C. After complete addition of diethyl acetonedicarboxylate, 484 g (5.09 mol) of trifluoroacetonitrile was passed into the reaction mixture. The reaction mixture was concentrated and the residue was poured into a mixture of 300 ml of concentrated hydrochloric acid and 1.8 L of water. The solid precipitate was collected to give 727 g (95%) of solid, mp 208.5°–210.5° C., which was a monohydrate of the desired product.

Anal. Calc'd. for $C_9H_8F_3NO_4 \cdot H_2O$; C, 40.16; H, 3.74; N, 5.20. Found: C, 40.02 H, 3.56; N, 5.37.

EXAMPLE 2

Methyl 4,6-dihydroxy-2(trifluoromethyl)-3-pyridinecarboxylate

To a well stirred mixture of 84.35 g (0.484 mol) of dimethyl acetonedicarboxylate, 200 ml of saturated sodium acetate, and 400 ml of ethanol at 70° C. was passed 49 g of trifluoroacetonitrile in 4 hours. The reaction mixture was cooled and poured into a mixture of 100 ml of concentrated HCl and 1000 g of ice. The insoluble material was collected to give 28.7 g (25%) of product: mp 235°–238.5° C. (dec).

Anal. Calc'd. for $C_8H_6F_3NO_4$: C, 40.56; H, 2.55; N, 5.91; Found: C, 40.55; H, 2.59: N, 5.88.

PPREPARATION OF 4,6-DIALKOXY PYRIDINE MONOCARBOXYLATES

The following Examples 3–7 show the preparation of 4,6-dialkoxy pyridine monocarboxylates by alkylation of the corresponding 4,6-dihydroxy compounds above.

EXAMPLE 3

Methyl 4,6-dimethoxy-2-(trifluoromethyl)-3-pyridinecarboxylate

A mixture of 14.43 g (0.061 mol) of product of Example 2, 16.8 g (0.122 mol) of potassium carbonate, 59 g of methyl iodide and 100 ml of acetone was held at reflux for 16.5 hours. The reaction mixture was poured into water and extracted with ether. The ether extracts were washed with 10% sodium hydroxide, dried and concentrated under reduced pressure. The residue was chromatographed on 50 g of silica gel. The first fraction, obtained by eluting with 1 L of ethyl acetate cyclohexane (1:4 v/v), was 10.47 g (64.8%) of the desired product: mp 85°–87.5° C.

Anal. Calc'd. for $C_{10}H_{10}F_3NO_4$: C, 45.28; H, 3.80; N, 5.28; Found: C, 45.42: H, 3.83; N, 5.24.

EXAMPLE 4

Ethyl 4,6-dimethoxy-2-(trifluoromethyl)-3-pyridinecarboxylate

A mixture of 50.2 g (0.2 mol) of product of Example 1, 45.2 g (0.4 mol) of potassium carbonate, 113.6 g (0.8 mol) of methyl iodide and 200 ml of acetone was held at reflux for 3 days, cooled and filtered. The filtrate was concentrated and the residue was dissolved in ether and chromatographed on silica gel. The first 2 L of eluate (ethyl acetate-cyclohexane 1:4) gave 41 g of solid which was recrystallized from hexane to give 36 g (64.5%) of Product: mp 78.5°–80.5° C.

Anal. Calc'd. for $C_{11}H_{12}F_3NO_4$: C, 47.31; H, 4.33; N, 5.02; Found: C, 47.51; H, 4.37; N, 4.99.

EXAMPLE 5

Ethyl 4,6-di-(n-butoxy)-2-(trifluoromethyl)-3-pyridinecarboxylate

A mechanically stirred mixture of 22.6 g (0.09 mol) of product of Example 1, 99 g of butyl iodide, 24.84 g of potassium carbonate and 250 ml of acetone was held at reflux for 26 hours and filtered. The acetone filtrate was concentrated and the residue was dissolved in ether. The ether solution was washed with water, dried, and concentrated. The residue was kugelrohr distilled at 0.3 torr to give 32.5 g (99%) of product, $n_D^{25}$ 1.4543.

Anal. Calc'd. for $C_{17}H_{24}F_3NO_4$: C, 56.19; H, 6.66; N, 3.86; Found: C, 56.26; H, 6.66; N, 3.84.

EXAMPLE 6

Ethyl 4,6-diisopropoxy-2-(trifluoromethyl)-3-pyridinecarboxylate

A mixture of 37.3 g of product of Example 1, 41 g of potassium carbonate, 99 g of 2-iodopropane and 300 ml of acetone was held at reflux for 21 hours. The reaction mixture was filtered. The acetone filtrate was concentrated. The residue was taken into ether and the ether solution was washed with 10% sodium hydroxide, dried, and concentrated. The residue was kugelrohr distilled to give 48.8 g (98%) of product, $n_D^{25}$ 1.4491.

Anal. Calc'd. for $C_{15}H_{20}F_3NO_4$: C, 53.72; H, 6.01; N, 4.18; Found: C, 53.77; H, 6.02; N, 4.15.

EXAMPLE 7

Ethyl 4,6-diethoxy-2-(trifluoromethyl)-3-pyridinecarboxylate

This material was prepared in 82.9% yield from product of Example 1 (1 eq), $K_2CO_3$ (2 eq) and excess ethyl iodide. The reaction mixture was refluxed in acetone for 18 hours and filtered. The filtrate was concentrated. The residue was dissolved in ether. The ether solution was washed with 10% $K_2CO_3$, dried ($MgSO_4$) and concentrated to give the product as an oil, $n_D^{25}$ 1.4534.

Anal. Calc'd. for $C_{13}H_{16}F_3NO_4$: C, 50.82; H, 5.24; Found: C, 50.79; H, 5.27.

PREPARATION OF 4,6-DIALKOXY PYRIDINE MONOCARBOXYLIC ACIDS

The following Examples 8–10 illustrate the preparation of acid compounds of this invention by hydrolysis of the ester compounds prepared above, while Example 11 illustrates esterification of an acid so obtained.

EXAMPLE 8

4,6-Diisopropoxy-2-(trifluoromethyl)-3-pyridinecarboxylic acid

A mixture of 9.5 g (0.0283 mol) of product of Example 6, 10 g of KOH and 150 ml of methanol was held at reflux for 16 hours. Methanol was removed under reduced pressure. The residue was treated with 300 ml of water and extracted with ether. The aqueous layer was poured into 50 ml of concentrated HCl and extracted with ether. The ether extract was concentrated. The residual solid (7.7 g) was recrystallized from hexane-ether to give 6.4 g (73.6%) of acid product: mp 147°–150° C.

Anal. Calc'd. for $C_{13}H_{16}F_3NO_4$: C, 50.81; H, 5.25; N, 4.56; Found: C, 50.80; H, 5.25; N, 4.54.

EXAMPLE 9

4,6-Dimethoxy-2-(trifluoromethyl)-3-pyridinecarboxylic acid

A mixture of 7.0 g (0.0264 mol) of product of Example 3, 30 ml of 10% sodium hydroxide and 10 ml of methanol was held at reflux for 18 hours, cooled and extracted with ether. The aqueous layer was made acidic and the precipitate was collected and dissolved in ether. The ether solution was dried and mixture was concentrated. The residual solid was recrystallized from hexane-ether to give 5.5 g (83%) of solid, mp 194°–197.5° C.

Anal. Calc'd. for $C_9H_8F_3NO_4$: C, 43.04; H, 3.21; N, 5.58; Found: C, 43.05; H, 3.25; N, 5.56.

EXAMPLE 10

4,6-Dibutoxy-2-trifluoromethyl-3-pyridinecarboxylic acid

A mixture of 25.6 g (0.0705 mol) of product of Example 5, 20 g of KOH and 250 ml of methanol was held at reflux for 16 hours. The reaction mixture was concentrated under reduced pressure to give a solid. This solid was dissolved in water (250 ml) and extracted with ether. Three layers were separated. The top layer (ether) was discarded. The bottom two layers were acidified with 100 ml of concentrated HCl. The organic layer was separated and extracted into ether. The ether extracts were dried and concentrated to give 21.2 g (89%) of solid which was crystallized from hexane at low temperature to give 5.1 g of pure product: mp 90°–93.5° C. and 5.1 g of second crop, mp 89°–92.5° C.

Anal. Calc'd. for $C_{15}H_{20}F_3NO_4$: C, 53.72; H, 6.01; N, 4.18; Found: C, 53.55; H, 6.00: N, 4.16.

EXAMPLE 11

Isopropyl 4,6-dibutoxy-2-(trifluoromethyl)-3-pyridinecarboxylate

A mixture of 5.0 g (0.015 mol) of product of Example 10 and 20 ml of thionyl chloride was held at reflux until gas evolution ceased. The reaction mixture was concentrated. The residue was heated with 10 ml of isopropanol for 2 hours and concentrated to give the isopropyl ester as an oil, $n_D^{25} = 1.4530$.

Anal. Calc'd. for $C_{18}H_{26}F_3NO_4$: C, 57.29; H, 6.94; Found: C, 57.27; H, 6.98.

PREPARATION OF 3,5-PYRIDINE DICARBOXYLIC ACID MONOESTERS

The following Examples 12–14 illustrate the carboxylation of monoesters previously prepared above with $CO_2$ to obtain a second carboxylic acid group at the 5-position on the pyridine ring.

EXAMPLE 12

4,6-Dimethoxy-2-(trifluoromethyl)-3,5-pyridinedicarboxylic acid 3-ethyl ester

The crude acid was obtained in 95% yield from 0.465 mol of LDA and 0.105 mol of product of Example 4 according to the following general procedure:

To a −78° C. solution of 1 to 2.5 eq of LDA in DME was added a solution of 1 eq of the monocarboxylate in dry DME. The resulting dark colored solution was stirred for 30 minutes at −78° C. To the above solution was added excess of dry ice. The reaction mixture was stirred at −78° C. for 15 minutes and warmed to room temperature in 1 hour. The reaction mixture was poured into ice water (100 ml) and extracted with ether. The aqueous layer was made acidic. The oil precipitate was extracted with ether. The ether extract was dried ($MgSO_4$) and concentrated in vacuo to give the desired product.

EXAMPLE 13

4,6-Diisopropoxy-2-(trifluoromethyl)-3,5-pyridinedicarboxylic acid 3-ethyl ester This material was obtained in 74% yield from 0.0716 mol of LDA and 0.0298 mol of product of Example 6 according to the above general procedure of Example 12 as a solid: mp 63°–65° C.

Anal. Calc'd. for $C_{16}H_{20}F_3NO_6$: C, 50.66; H, 5.31; Found: C, 50.93; H, 5.29.

EXAMPLE 14

4,6-Diethoxy-2-(trifluoromethyl)-3,5-pyridinedicarboxylic acid 3-ethyl ester

The crude acid was obtained in 66.8% yield from 0.427 mol of LDA and 0.146 mol of product of Example 7 according to the above general procedure. After crystallization from hexane it was used without further purification.

PREPARATION OF 4,6-DIALKOXY PYRIDINE DIESTERS

The following Examples 15–19 illustrate the esterification of monoesters produced above.

EXAMPLE 15

3-Ethyl 5-methyl 4,6-dimethoxy-2-(trifluoromethyl)-3,5-pyridinedicarboxylate This material was obtained in 42% yield from the product of Example 12, thionyl chloride and methanol according to the following general procedure as an oil; $n_D^{25}$ 1.4615. A 5.0 g of the starting acid was refluxed with excess thionyl chloride until the reaction was completed. Excess thionyl chloride was removed in vacuo. The residual acid chloride was refluxed with an excess of appropriate alcohol for 2–4 hours and concentrated to give the desired product. The crude product was dissolved in ether and the ether solution was washed with 10% $K_2CO_3$, dried ($MgSO_4$) and concentrated. The residue may be purified by either a kugelrohr distillation or HPLC separation.

Anal. Calc'd. for $C_{13}H_{14}F_3NO_6$: C, 46.30; H, 4.18; N, 4.15; Found: C, 46.32; H, 4.24; N, 3.96.

EXAMPLE 16

Dimethyl 2,4-diethoxy-6-(trifluoromethyl)-3,5-pyridinedicarboxylate

A mixture of 9.01 g (0.161 mol) of 85% KOH, 11.84 g (0.037 mol) of the product of Example 14, 150 ml of ethanol and 10 ml of water was held at reflux for 24 hours and poured into 250 ml of water containing 50 ml of concentrated HCl. The mixture was extracted with ether. The ether extract was dried ($MgSO_4$) and concentrated to give 11.84 g of a solid. A portion (8.0 g) of this solid was held at reflux with 150 ml of thionyl chloride for 3 hours and concentrated in vacuo. The residue was refluxed with 150 ml of methanol for 2 hours and concentrated. The residue was purified by HPLC using 5% EtOAc-cyclohexane as eluant to give 3.03 g (34.8%) of product as an oil; $n_D^{25}$ 1.4566.

Anal. Calc'd. for $C_{14}H_{16}F_3NO_4$: C, 47.87; H, 4.59; N, 3.99; Found: C, 47.87; H, 4.76; N, 3.81.

EXAMPLE 17

Diethyl 2,4-diethoxy-6-(trifluoromethyl)-3,5-pyridinedicarboxylate

This material was prepared from the product of Example 14 and ethanol according to the general procedure set out in Example 15. The crude product was dissolved in ether. The ether solution was washed with 10% $K_2CO_3$, dried over $CaSO_4$, and concentrated in vacuo to give 4.41 g (80%) of product as an oil: $n_D^{25}$ 1.4555.

Anal. Calc'd. for $C_{16}H_{20}F_3NO_6$: C, 50.66; H, 5.31; N, 3.69; Found: C, 51.20; H, 5.49; N, 3.71.

EXAMPLE 18

3-Ethyl 5-methyl 4,6-diethoxy-2-(trifluoromethyl)-3,5-pyridinedicarboxylate

This material was obtained from the product of Example 14 and methanol according to the general procedure of Example 15. The crude product was purified by a 10% $K_2CO_3$ wash to give 3.78 g (72.7%) of product as a solid: mp 46°–48° C.

Anal. Calc'd. for $C_{15}H_{18}F_3NO_6$: C, 49.32; H, 4.97; N, 3.83; Found: C, 49.62; H, 4.93; N, 3.83.

EXAMPLE 19

3-Ethyl 5-isopropyl 4,6-diisopropoxy-2-(trifluoromethyl)-3,5-pyridinedicarboxylate This material was prepared in 70% yield from the product of Example 13 and isopropanol according to the above general procedure as an oil; $n_D^{25}$ 1.4508.

Anal. Calc'd. for $C_{19}H_{26}F_3NO_3$: C, 54.15; H, 6.22, Found: C, 53.81; H, 6.08.

ALTERNATE PREPARATION OF DIALKOXY DIESTERS

The following Examples 20–21 show the formation of diesters from monoesters by reaction with an alkyl chloroformate.

EXAMPLE 20

Diethyl 4,6-dimethoxy-2-(trifluoromethyl)-3,5-pyridinedicarboxylate

To a cold (−78° C.) solution of LDA, from 0.0329 mol (4.6 ml) of diisopropylamine, 0.0336 mol of n-BuLi, and 40 ml of DME was added a solution of 8.37 g (0.03 mol) of product of Example 4 in 29 ml of DME. The reaction mixture turned yellowish green initially, then to orange. This solution was stirred at −78° C. for 1 hour and treated with 10 ml of ethyl chloroformate. After 15 minutes stirring at −78° C., the orange color turned yellow. The reaction mixture was poured into a mixture of 20 ml of concentrated HCl and 100 ml of ice water. The organic material was extracted into ether (2×200 ml). The ether extract was dried and concentrated to give 5.5 g of an oil which was kugelrohr distilled at 0.1 torr (pot temperature 80°–120° C.) to give 5.0 g of oil which contained about 10% starting material. The oil was distilled through a short path still at 0.1 torr to give 1.9 (18%) of product, bp 132°–133°C.; $n_D^{25}$ 1.4386.

Anal. Calc'd. for $C_{14}H_{16}F_3NO_6$: C, 47.87; H, 4.59; N, 3.99; Found: C, 47.83; H, 4.59; N, 3.99.

EXAMPLE 21

Diethyl 2,4-diisopropoxy-6-(trifluoromethyl)-3,5-pyridinedicarboxylate

To a −78° C. solution of 0.021 mol of LDA in DME (30 ml) was added a solution of 4.65 g (0.014 mol) of product of Example 6 in 20 ml of DME. The resulting solution was stirred for 10 minutes and treated with 2.7 ml (0.035 mol) of ethyl chloroformate. After stirring at −78° C. for 30 minutes the reaction mixture was warmed to room temperature in 30 minutes and poured into 50 ml of water. The mixture was extracted with ether. The ether extract was washed with 10% $K_2CO_3$, dried over $CaSO_4$ and concentrated. The residue was first kugelrohr distilled at 0.15 torr (pot temperature 55° C.) to remove low boiling material (1.08 g), then distilled at 164°–173° C. (0.15 torr) to give 1.95 g (34.5%) of product as an oil.

Anal. Calc'd. for $C_{18}H_{24}F_3NO_6$: C, 53.07; H, 5.94; Found: C, 53.14; H, 5.96.

PREPARATION OF OTHER 6-SUBSTITUTED-3-PYRIDINECARBOXYLIC ACID DERIVATIVES

The following Examples 22–30 show the preparation of other 4,6-dialkoxy-3-pyridinecarboxylate derivatives of the present invention among the substituents at the 5-position on the pyridine ring are amide groups, nitriles, and substituted alkyl groups.

EXAMPLE 22

Ethyl 5-aminocarbonyl-4,6-dimethoxy-2-(trifluoromethyl)-3-pyridinecarboxylate

A mixture of 8.0 g (0.025 mol) of product of Example 12 and 10 ml of thionyl chloride was refluxed until gas evolution ceased. The reaction mixture was concentrated in vacuo. The residue was dissolved in ether and the ether solution was added to a 25 ml flask containing 10 ml of liquid ammonia. A solid formed immediately and was filtered. The solid (8.3 g) was washed with water to give 5.4 g (67.9%) of crude product which was used without further purification.

EXAMPLE 23

Ethyl 5-aminocarbonyl-4,6-diethoxy-2-(trifluoromethyl)-3-pyridinecarboxylate

A mixture of 10.0 g (0.028 mol) of product of Example 14 and 20 ml of thionyl chloride was held at reflux until gas evolution ceased. The reaction mixture was concentrated to give 9.62 g (91.4%) of the acid chloride. The material was dissolved in 50 ml of ether. The ether solution was added to a three necked flask equipped with dry ice condenser and containing 75 ml of liquid ammonia. The reaction mixture was stirred for 18 hours while solvent and excess ammonia was allowed to evaporate. The resulting solid was stirred with water and filtered to give 8.17 g (89.6%) of product as a tan solid: mp 103°–105° C.

Anal. Calc'd. for $C_{14}H_{17}F_3N_2O_5$: C, 48.00; H, 4.89; N, 8.00; Found: C, 48.28; H, 5.11; N, 8.05.

EXAMPLE 24

Ethyl 5-cyano-4,6-diethoxy-2-(trifluoromethyl)-3-pyridinecarboxylate

A mixture of 6.17 g (0.018 mol) of product of Example 23 and 100 ml of $POCl_3$ was held at reflux for 7 hours and concentrated in vacuo. The residue was poured into water and extracted with ether. The ether extract was washed with 15% $K_2CO_3$, dried ($MgSO_4$) and concentrated to give 1.44 g (24.6%) of product as an oil; $n_D^{25}$ 1.4677.

Anal. Calc'd. for $C_{14}H_{15}F_3H_2O_4$: C, 50.61; H, 4.55; N, 8.43; Found: C, 50.53: H, 4.62; N, 8.21.

EXAMPLE 25

Ethyl 5-cyano-4,6-dimethoxy-2-(trifluoromethyl)-3-pyridinecarboxylate

This material was obtained in 84.9% yield from the product of Example 22 (0.014 mol) and 100 ml of $POCl_3$ by a procedure similar to that in Example 24 as a solid: mp 32°–34° C.

Anal. Calc'd. for $C_{12}H_{11}F_3N_2O_4$: C, 47.38; H, 3.64; N, 9.21; Found: C, 47.45; H, 3.62; N, 8.92.

EXAMPLE 26

Ethyl 4,6-dimethoxy-5-(methoxyethoxymethyl)-2-(trifluoromethyl)-3-pyridinecarboxylate To a −78° C. solution of 0.064 mol of LDA (prepared from 0.064 mol of BuLi and 9.0 ml of diisopropylamine) in 40 ml of DME was added a solution of 14.7 g (0.0527 mol) of product from Example 4 in 40 ml of dry DME by a syringe. After the resulting orange solution had been stirred for 20 minutes the reaction mixture was treated with 14 ml of methoxyethoxymethyl chloride (MEM chloride) at once. The resulting dark colored solution was stirred at −78° C. for 30 minutes and warmed to 20° C. in 1 hour. The reaction mixture was poured into 300 ml of water containing 30 ml of concentrated HCl. The mixture was extracted twice with 300 ml of ether. The ether extract was dried and concentrated to give an oil which was kugelrohr distilled at 1 torr (pot temperature 140° C.) to give 17.0 g(88%) of product as a colorless oil; $n_D^{25}$ 1.4605.

Anal. Calc'd. for $C_{15}H_{20}F_3NO_6$: C, 49.03; H, 5.49; N, 3.81; Found: C, 49.06; H, 5.50; N, 3.80.

EXAMPLE 27

Ethyl 5-chloromethyl-4,6-dimethoxy-2-(trifluoromethyl)-3-pyridinecarboxylate

To a solution of 15.5 g (0.0289 mol) of product of Example 26 in 30 ml of $CH_2Cl_2$ cooled in a ice water bath was added 12.0 g of titanium tetrachloride. The reaction mixture turned brown with formation of a white precipitate. After stirring at 10°–15° C. for 20 minutes, then at 20° C. for 20 minutes, the reaction mixture was poured into 70 ml of 6N HCl. The $CH_2Cl_2$ layer was separated, dried ($MgSO_4$) and concentrated. The residue was kugelrohr distilled at 2 torr (pot temperature 140° C.) to give 9.1 g (97%) of product as a colorless liquid: $n_D^{25}$ 1.4738.

Anal. Calc'd. for $C_{12}H_{13}ClF_3N_2O_4$: C, 43.98; H, 3.99; N, 4.27; Cl, 10.82; Found: C, 43.97; H, 4.01; N, 4.23; Cl; 10.78.

EXAMPLE 28

[5-Carbethoxy-2,4-(dimethoxy)-6-(trifluoromethyl)-3-pyridyl]acetonitrile

A mixture of 3.2 g (0.00978 mol) of product of Example 27 and 1.13 g (0.0179 mol) of sodium cyanide and 30 ml of DMF was stirred for 1.5 hours and poured into 500 ml of water. The organic phase was extracted into ether (2×100 ml). The ether extract was dried ($MgSO_4$) and concentrated. The residue was kugelrohr distilled at 0.05 torr (pot temperature 160° C.) to give 2.4 g (77%) of product as a liquid. $n_D^{25}$ 1.4690.

Anal. Calc'd. for $C_{13}H_{13}F_3N_2O_4$: C, 49.06; H, 4.11; N, 8.80; Found: C, 49.28; H, 4.18; N, 8.73.

EXAMPLE 29

Ethyl [5-carbethoxy-2,4-dimethoxy-6-(trifluoromethyl)-3-pyridyl]acetate

A mixture of 1.5 g (4.71 mol) of product of Example 29, 60 ml of concentrated sulfuric acid and 50 ml of dry ethanol was held at reflux for 2 days. The reaction mixture was concentrated. The residue was dissolved in ether and washed with saturated NaHCO$_3$ (50 ml), dried (MgSO$_4$) and concentrated. The residue was chromatographed by HPLC using 5% ethyl acetate/cyclohexane as eluant. The first fraction (retention time 12-14 minutes) gave an oil which was kugelrohr distilled at 0.8 torr (pot temperature 210° C.) to give 0.9 g (52.3%) of product as a colorless liquid, n$_D^{25}$ 1.4601.

Anal. Calc'd. for C$_{15}$H$_{16}$F$_3$NO$_6$: C, 49.31; H, 4.97; N, 3.83; Found: C, 49.59; H, 4.94; N, 3.61.

The compounds of this invention wherein R$_1$ is selected from difluoromethyl and monofluoromethyl radicals may be prepared by hydrogenation of the corresponding compounds in which R$_1$ to be selected from a chlorofluorinated methyl radical using palladium on charcoal as catalyst.

PRE-EMERGENT HERBICIDE EXAMPLES

As noted above, many of the compounds of this invention have been found to be effective as herbicides, particularly those with ester substitutions at the 3-position and ester, nitrile, lower cyanoalkyl, or alkoxycarbonylalkyl substitution at the 5-position, usually as pre-emergent herbicides. Table 1 summarizes results of tests conducted to determine the pre-emergent herbicidal activity of the compounds of this invention on common weeds.

The pre-emergent tests are conducted as follows:

Top soil is placed in aluminum pans and compacted to a depth of 0.95 to 1.27 cm. from the top of the pan. On the top of the soil is placed a predetermined number of seeds or vegetative propagules of various plant species. The soil required to level fill the pans after seeding or adding vegetative propagules is weighed into a pan. A known amount of the active ingredient dissolved in an appropriate solvent (usually acetone) is thoroughly mixed with the soil, and the herbicide/soil mixture is used as a cover layer for prepared pans. In Table 1 below the amount of active ingredient is equal to the rate of 11.2 kg/ha. After treatment, the pans are moved into a greenhouse bench where they are watered from below as needed to give adequate moisture for germination and growth.

Approximately 10-14 days (usually 11 days) after seeding and treating, the pans are observed and the results recorded. In some instances, a second observation is made approximately 24-28 days after seeding and treating, and these observations are indicated in the following tables by an asterisk (*) immediately following the Example number.

Table 1 below summarizes the results of the pre-emergent herbicidal activity tests of compounds The herbicidal rating is obtained by means of a fixed scale based on the percent inhibition of each plant species. The symbols in the Table are defined as follows:

| % Inhibition | Rating |
|---|---|
| 0-24 | 0 |
| 25-49 | 1 |
| 50-74 | 2 |
| 75-100 | 3 |
| Not planted | — |
| Species planted, | N |

| % Inhibition | Rating |
|---|---|
| no data | |

WEED-PLANT HERBICIDE ACTIVITY

The plant species usually regarded as weeds which are utilized in one set of tests, the data for which are shown in Table 1, are identified by letter headings above the columns in accordance with the following legend:

A—Canada Thistle*
B—Cocklebur
C—Velvetleaf
D—Morningglory
E—Common Lambsquarters
F—Pennsylvania Smartweed
G—Yellow Nutsedge*
H—Quackgrass*
I—Johnsongrass*
J—Downy Brome
K—Barnyardgrass
* Grown from vegetative propagules

TABLE 1

| Example No. | Kg/ha | A | B | C | D | E | F | G | H | I | J | K |
|---|---|---|---|---|---|---|---|---|---|---|---|---|
| 15 | 11.2 | — | 1 | 3 | 3 | 3 | — | 1 | 3 | 1 | 3 | 3 |
| 16 | 11.2 | 0 | 0 | 2 | 3 | 3 | 3 | 2 | 3 | 0 | 3 | 3 |
| 17 | 11.2 | — | 0 | 1 | 2 | 3 | — | 0 | 0 | 0 | 3 | 3 |
| 18 | 11.2 | — | 1 | 1 | 2 | 3 | — | 0 | 1 | 0 | 3 | 3 |
| 19 | 11.2 | 0 | 0 | 0 | 0 | 0 | — | 0 | 0 | 0 | 0 | 0 |
| 20 | 11.2 | 1 | 2 | 3 | 3 | 3 | 3 | 0 | 3 | 0 | 3 | 3 |
| 20* | 11.2 | 0 | 0 | 2 | 3 | 3 | 3 | 0 | 3 | 0 | 3 | 3 |
| 21 | 11.2 | 0 | 0 | 0 | 0 | 1 | 0 | 0 | 0 | 0 | 3 | 3 |
| 23 | 11.2 | — | 0 | 0 | 0 | 0 | — | 0 | 0 | 0 | 0 | 0 |
| 24 | 11.2 | — | 0 | 1 | 0 | 0 | — | 0 | 0 | 0 | 3 | 3 |
| 25 | 11.2 | — | 0 | 0 | 0 | 2 | 0 | 0 | 0 | 0 | 1 | 3 |
| 26 | 11.2 | 0 | 0 | 0 | 0 | 1 | 0 | 0 | 0 | 0 | 0 | 2 |
| 27 | 11.2 | 0 | 0 | 0 | 0 | 3 | 1 | 0 | 0 | 1 | 0 | 2 |
| 28 | 11.2 | 0 | 0 | 0 | 0 | 3 | — | 0 | 0 | 0 | 3 | 3 |
| 29 | 11.2 | — | 0 | 0 | 0 | 2 | 0 | 0 | 0 | 3 | 0 | 1 |

CROP PLANT HERBICIDE ACTIVITY

The compounds were further tested by utilizing the above procedure on the following plant species, i.e., on weeds in the presence of crop plants.

L—Soybean
M—Sugarbeet
N—Wheat
O—Rice
P—Grain Sorghum
B—Cocklebur
Q—Wild Buckwheat
D—Morningglory
R—Hemp Sesbania
E—Common Lambsquarters
F—Pennsylvania Smartweed
C—Velvetleaf
J—Downy Brome
S—Panicum spp.
K—Barnyardgrass
T—Large Crabgrass The results are summarized in Table 2.

TABLE 2

PRE-EMERGENT ACTIVITY FOR WEEDS IN CROP PLANTS

| Example No. | Kg/ha | L | M | N | O | P | B | Q | D | R | E | F | C | J | S | K | T |
|---|---|---|---|---|---|---|---|---|---|---|---|---|---|---|---|---|---|
| 15 | 5.6 | 1 | 3 | 3 | 3 | 3 | 0 | 3 | 3 | 2 | 3 | 3 | 3 | 3 | 3 | 3 | 3 |
|  | 1.12 | 1 | 2 | 0 | 0 | 3 | 0 | 3 | 2 | 1 | 3 | 3 | 0 | 2 | 3 | 3 | 3 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
|  | 0.0112 | 0 | 0 | 0 | 0 | 0 | 0 | 0 | 0 | 0 | 0 | 0 | 0 | 0 | 0 | 0 | 0 |
| 16 | 5.6 | 1 | 3 | 3 | 3 | 3 | 1 | 3 | 3 | 3 | 3 | 3 | 2 | 3 | 3 | 3 | 3 |
|  | 1.12 | 0 | 2 | 0 | 1 | 0 | 0 | 0 | 0 | 0 | 0 | 0 | 0 | 0 | 1 | 2 | 1 |
|  | 0.28 | 0 | 0 | 0 | 0 | 0 | 0 | 0 | 0 | 0 | 0 | 0 | 0 | 0 | 0 | 1 | 0 |
|  | 0.056 | 0 | 0 | 0 | 0 | 0 | 0 | 0 | 0 | 0 | 0 | 0 | 0 | 0 | 0 | 0 | 0 |
| 17 | 5.6 | 0 | 2 | 1 | 1 | 3 | 0 | 3 | 2 | 1 | 3 | 3 | 0 | 3 | 3 | 3 | 3 |
|  | 1.12 | 0 | 0 | 0 | 0 | 0 | 0 | 0 | 0 | 0 | 2 | 1 | 0 | 0 | 0 | 0 | 2 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 18 | 5.6 | 0 | 3 | 3 | 3 | 3 | 0 | 3 | 2 | 2 | 3 | — | 1 | 3 | 3 | 3 | 3 |
|  | 1.12 | 0 | 1 | 0 | 0 | 0 | 0 | 0 | 0 | 0 | 3 | — | 1 | 0 | 1 | 2 | 3 |
|  | 0.28 | 0 | 0 | 0 | 0 | 0 | 0 | 0 | 0 | 0 | 0 | — | 0 | 0 | 0 | 0 | 0 |
|  | 0.056 | 0 | 0 | 0 | 0 | 0 | 0 | 0 | 0 | 0 | 0 | — | 0 | 0 | 0 | 0 | 0 |
| 20 | 5.6 | 0 | 3 | 1 | 3 | 3 | 0 | 2 | 3 | 2 | 3 | 3 | 2 | 2 | 3 | 3 | 3 |
|  | 1.12 | 0 | 0 | 0 | 0 | 0 | 0 | 0 | 1 | 1 | 1 | 0 | 0 | 0 | 0 | 0 | 1 |
|  | 0.28 | 0 | 0 | 0 | 0 | 0 | 0 | 0 | 0 | 0 | 0 | 0 | 0 | 0 | 0 | 0 | 0 |
|  | 0.056 | 0 | 0 | 0 | 0 | 0 | 0 | 0 | 0 | 0 | 0 | 0 | 0 | 0 | 0 | 0 | 0 |
| 21 | 5.6 | 0 | 0 | 0 | 0 | 0 | 0 | 0 | 0 | 0 | 3 | 0 | 2 | 0 | 3 | 3 | 3 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 24 | 5.6 | 0 | 3 | 0 | 0 | 2 | 0 | 0 | 0 | 0 | 0 | 0 | 0 | 0 | 1 | 3 | 1 |
|  | 1.12 | 0 | 0 | 0 | 0 | 0 | 0 | 0 | 0 | 0 | 0 | 0 | 0 | 0 | 0 | 0 | 0 |
|  | 0.28 | 0 | 0 | 0 | 0 | 0 | 0 | 0 | 0 | 0 | 0 | 0 | 0 | 0 | 0 | 0 | 0 |
| 28 | 5.6 | 0 | 2 | 0 | 1 | 1 | 2 | 1 | 0 | 1 | 3 | — | 1 | 1 | 2 | 3 | 3 |
|  | 1.12 | 0 | 1 | 1 | 0 | 0 | 0 | 0 | 0 | 0 | 2 | — | 1 | 0 | 1 | 3 | 3 |
|  | 0.28 | 0 | 0 | 0 | 0 | 0 | 0 | 0 | 0 | 0 | 0 | — | 0 | 0 | 0 | 0 | 0 |

POST-EMERGENT HERBICIDE EXAMPLES

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan, is removed individually to a spraying chamber and sprayed by means of an atomizer, operating at a spray pressure of 170.3 kPa (10 psig) at the application rates noted. In the spray solution is an amount of an emulsifying agent mixture to give a spray solution or suspension which contains about 0.4% by weight of the emulsifier. The spray solution or suspension contains a sufficient amount of the candidate chemical in order to give application rates of the active ingredient corresponding to those shown in the Tables while applying a total amount of solution or suspension equivalent to 1870 L/Ha (200 gallons/acre). The pans were returned to the greenhouse and watered as before and the injury to the plants as compared to the control is observed at approximately 10–14 days (usually 11 days). The post-emergent herbicidal activity index used in Table 3 is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — |
| Species planted, no data | N |

TABLE 3

POST-EMERGENT ACTIVITY FOR WEEDS

| Example No. | Kg/ha | A | B | C | D | E | F | G | H | I | J | K |
|---|---|---|---|---|---|---|---|---|---|---|---|---|
| 15 | 11.2 | — | 0 | 0 | 0 | 0 | 0 | 0 | 0 | 0 | 0 | 0 |
| 16 | 11.2 | N | 0 | 1 | 0 | 0 | 0 | 0 | 0 | 0 | 0 | 0 |
| 17 | 11.2 | — | 0 | 0 | 0 | 2 | 0 | 0 | 0 | 0 | 0 | 0 |
| 18 | 11.2 | — | 0 | 0 | 0 | 0 | — | 0 | 0 | 0 | 0 | 0 |
| 19 | 11.2 | 0 | 0 | 0 | 0 | 0 | — | 0 | 0 | 0 | 0 | 0 |
| 20 | 11.2 | 0 | 0 | 0 | 0 | 0 | N | 0 | 0 | 1 | 0 | 1 |
| 21 | 11.2 | 0 | 0 | 0 | 0 | 0 | 0 | 0 | 0 | 0 | 0 | 0 |
| 23 | 11.2 | — | 0 | 0 | 0 | 0 | — | 0 | 0 | 0 | 0 | 0 |
| 24 | 11.2 | — | 0 | 0 | 0 | 0 | N | 0 | 0 | 0 | 0 | 0 |
| 25 | 11.2 | — | 0 | 0 | 0 | 0 | — | 0 | 0 | 0 | 0 | 0 |
| 26 | 11.2 | 0 | 0 | 0 | 0 | 0 | 0 | 0 | 0 | 0 | 0 | 0 |
| 27 | 11.2 | 0 | 0 | 0 | 0 | 0 | 0 | 0 | 0 | 0 | 0 | 0 |
| 28 | 11.2 | 0 | 0 | 0 | 0 | 0 | — | 0 | 0 | 0 | 0 | 0 |
| 29 | 11.2 | — | 0 | 0 | 0 | 0 | — | 0 | 0 | 0 | 0 | 0 |

The above tables illustrate one aspect of the present invention, that is, the use of the compounds of the invention to kill or injure undesirable plants, e.g., weeds.

As can be seen from the data above, some of the compounds appear to be quite safe on certain crops and can thus be used for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of theses.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan) and polyoxyethylene derivatives of castor oil. Preferred dispersants are methyl cellulose, polyvinyl alcohol, sodium lignin sulfonates, polyoxyethylene/polyoxypropylene block copolymers, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, bentonite, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include chlorinated solvents, dimethylformamide, dimethylsulfoxide, N-methyl-pyrrolidone, hydrocarbons, and water-immiscible ethers, esters, or ketones. However, other high strength liquid concentrates may be formulted by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particules such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like, such as Heterocyclic Nitrogen/Sulfur Derivatives 2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium Ureas N-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl) aminocarbonyl]-benzenesulfonamide.

Carbamates/Thiolcarbamates

2-Chloroallyl diethyldithiocarbamate
2-(4-chlorobenzyl)N,N-diethylthiolcarbamate
Isopropyl N-(3-chlorophenyl) carbamate
s-2,3-dichloroallyl N,N-diisopropylthiolcarbamate
S-N,N-dipropylthiolcarbamate
S-propyl N,N-dipropylthiolcarbamate S-2,3,3-trichloroallyl N,N-diisopropylthiolcarbamate Acetamides/Acetanilides/Anilines/Amides 2-Chloro-N,N-diallylacetamide
N,N-dimethyl-2,2-diphenylacetamide
N-(2,4-dimethyl-5-[[(trifluoromethyl)sulfonyl]amino]-phenyl]acetamide
N-Isopropyl-2-chloroacetanilide
2′,6′-Diethyl-N-methoxymethyl-2-chloroacetanilide
2′-Methyl-6′-ethyl-N-(2-methoxyprop-2-yl)-2-chloroacetanilide
δ,δ,δ-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its salts.

Ethers 2,4-Dichlorophenyl-4-nitrophenyl ether
2-Chloro-δ,δ,δ-trifluoro-p-tolyl-3-ethoxy-4-nitrodiphenyl ether Miscellaneous 2,6-Dichlorobenzonitrile
Monosodium acid methanearsonate
Disodium methanearsonate
Methyl 2-[4-(2,4-dichlorophenoxy)phenoxy]propanoate
Butyl 2-[4-[(5-(trifluoromethyl)-2-pyridinyl)oxy]-phenoxy]-propanoate

| I. Emulsifiable Concentrates | | |
|---|---|---|
| | | Weight Percent |
| A. | Compound of Example No. 15 | 11.0 |
| | Free acid of complex organic phosphate or aromatic or aliphatic hydrophobe base (e.g., GAFAC RE-610, registered trademark of GAF Corp.) | 5.59 |
| | Polyoxyethylene/polyoxypropylene block copolymer with butanol (e.g., Tergitol XH, registered trademark of Union Carbide Corp.) | 1.11 |
| | Phenol | 5.34 |
| | Monochlorobenzene | 76.96 |
| | | 100.00 |
| B. | Compound of Example No. 16 | 25.00 |
| | Free acid of complex organic phosphate of aromatic or aliphatic hydrophobe base (e.g., GAFAC RE-610) | 5.00 |
| | Polyoxyethylaene/polyoxypropylene block copolymer with butanol (e.g., Tergitol XH) | 1.60 |
| | Phenol | 4.75 |
| | Monochlorobenzene | 63.65 |
| | | 100.00 |

| II. Flowables | | |
|---|---|---|
| | | Weight Percent |
| A. | Compound of Example No. 17 | 25.00 |
| | Methyl cellulose | 0.3 |
| | Silica Aerogel | 1.5 |
| | Sodium lignosulfonate | 3.5 |
| | Sodium N—methyl-N—oleyl taurate | 2.0 |
| | Water | 67.7 |
| | | 100.00 |
| B. | Compound of Example No. 20 | 45.0 |
| | Methyl cellulose | .3 |
| | Silica aerogel | 1.5 |
| | Sodium lignosulfonate | 3.5 |
| | Sodium N—methyl-N—oleyl taurate | 2.0 |
| | Water | 47.7 |
| | | 100.00 |

| III. Wettable Powders | | |
|---|---|---|
| | | Weight Percent |
| A. | Compound of Example No. 20 | 25.0 |
| | Sodium lignosulfonate | 3.0 |
| | Sodium N—methyl-N—oleyl-taurate | 1.0 |
| | Amorphous silica (synthetic) | 71.0 |
| | | 100.00 |
| B. | Compound of Example 18 | 80.0 |
| | Sodium dioctyl sulfosuccinate | 1.25 |
| | Calcium lignosulfonate | 2.75 |
| | Amorphous silica (synthetic) | 16.0 |
| | | 100.00 |
| C. | Compound of Example No. 15 | 10.0 |
| | Sodium lignosulfonate | 3.0 |
| | Sodium N—methyl-N—oleyl-taurate | 1.0 |
| | Kaolinite clay | 86.0 |
| | | 100.00 |

| IV. Dusts | | |
|---|---|---|
| | | Weight Percent |
| A. | Compound of Example No. 28 | 2.0 |
| | Attapulgite | 98.0 |
| | | 100.00 |
| B. | Compound of Example No. 16 | 60.0 |
| | Montmorillonite | 40.0 |
| | | 100.00 |
| C. | Compound of Example No. 18 | 30.0 |
| | Ethyleneglycol | 1.0 |
| | Bentonite | 69.0 |
| | | 100.00 |
| D. | Compound of Example No. 20 | 1.0 |
| | Diatomaceous earth | 99.0 |
| | | 100.00 |

| V. Granules | | |
|---|---|---|
| | | Weight Percent |
| A. | Compound of Example No. 21 | 15.0 |
| | Granular attapulgite (20/40 mesh) | 85.0 |
| | | 100.00 |
| B. | Compound of Example No. 20* | 30.0 |
| | Diatomaceous earth (20/40) | 70.0 |
| | | 100.00 |
| C. | Compound of Example No. 25 | 1.0 |
| | Ethylene glycol | 5.0 |
| | Methylene blue | 0.1 |
| | Pyrophyllite | 93.9 |
| | | 100.00 |
| D. | Compound of Example No. 28 | 5.0 |
| | Pyrophyllite (20/40) | 95.0 |

| -continued | |
|---|---|
| V. Granules | |
| | Weight Percent |
| | 100.00 |

Fertilizers useful in combination with the active ingredients include, for example, ammonium nitrate, urea, potash and superphosphate. Other useful additaments include materials in which plant orgnaism take root and grow such as compost, manure, humus, sand, and the like.

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or media in which vegetation may take root and grow, and includes not only earth but also compost, manure, muck, humus, sand, and the like, adapted to support plant growth.

Although the invention is described with respect to specific modifications, the details thereof are not to be construed as limitations.

What is claimed is:

1. A compound represented by the generic formula

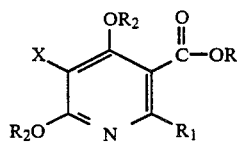

wherein:
R is selected from the group consisting of hydrogen, lower alkyl, lower alkenyl, lower alkynyl, haloalkyl, haloalkenyl;
$R_1$ is fluorinated methyl and chlorofluorinated methyl;
$R_2$ is selected from hydrogen and lower alkyl radicals; and
X is selected from

in which $R_3$ is hydrogen, or lower alkyl, lower alkenyl, lower alkynyl, or haloalkyl, and carbalkoxyalkyl.

2. A compound according to claim 1 wherein $R_2$ is lower alkyl having 1–4 carbon atoms.

3. A compound according to claim 2 wherein X is

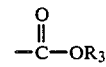

4. A compound according to claim 3 wherein R and $R_3$ are independently selected from lower alkyl radicals having 1–4 carbon atoms.

5. A herbicidal composition containing a carrier and a herbicidally effective amount of a compound represented by the generic formula

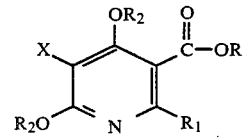

wherein:
R is selected from the group consisting of lower alkyl, lower alkenyl, lower alkynyl, haloalkyl, haloalkenyl;
$R_1$ is trifluoromethyl;
$R_2$ is a lower alkyl radical; and
X is selected from

in which $R_3$ is lower alkyl, lower alkenyl, lower alkynyl, or haloalkyl, and carbalkoxyalkyl.

6. A composition according to claim 5 wherein $R_2$ is lower alkyl having 1–4 carbon atoms.

7. A composition according to claim 6 wherein X is

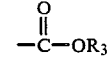

8. A composition according to claim 7 wherein R and $R_3$ are independently selected from lower alkyl radicals having 1–4 carbon atoms.

9. A method of controlling the growth of undesirable vegetation comprising applying to the plant locus an effective amount of a compound represented by the generic formula

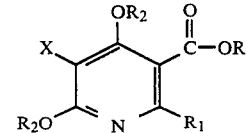

wherein:

R is selected from the group consisting of lower alkyl, lower alkenyl, lower alkynyl, haloalkyl, haloalkenyl;
$R_1$ is trifluoromethyl;
$R_2$ is a lower alkyl radicals; and
X is selected from $$\underset{\text{C}-OR_3}{\overset{\text{O}}{\|}}$$

in which $R_3$ lower alkyl, lower alkenyl, lower alkynyl, or haloalkyl, and carbalkoxyalkyl.

10. A method according to claim 9 wherein $R_2$ is lower alkyl having 1–4 carbon atoms.

11. A method according to claim 10 wherein X is $$\underset{\text{C}-OR_3}{\overset{\text{O}}{\|}}$$

12. A method according to claim 11 wherein R and $R_3$ are independently selected from lower alkyl radicals having 1–4 carbon atoms.

* * * * *